United States Patent
Bryndzia et al.

(10) Patent No.: US 9,684,092 B2
(45) Date of Patent: Jun. 20, 2017

(54) METHODS FOR ESTIMATING RESOURCE DENSITY BY INTEGRATING SEISMIC METHODS WITH FLUID DENSITY AND PRESSURE IN SHALE RESOURCE PLAYS

(71) Applicant: Shell Oil Company, Houston, TX (US)

(72) Inventors: Lubomyr Taras Bryndzia, Houston, TX (US); Saad Jamil Saleh, Sugar Land, TX (US); Calum Ian Macaulay, Houston, TX (US); Neil Robert Braunsdorf, Sugar Land, TX (US); Theodericus Johannes Henricus Smit, Rijswijk (NL); Ronny Hofmann, Houston, TX (US); Brian Harvey Hoffe, Calgary (CA); Ezequiel Francisco Gonzalez San Miguel, Katy, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/501,374

(22) Filed: Sep. 30, 2014

(65) Prior Publication Data

US 2015/0301219 A1     Oct. 22, 2015

Related U.S. Application Data

(60) Provisional application No. 61/885,225, filed on Oct. 1, 2013.

(51) Int. Cl.
| | | |
|---|---|---|
| *G01J 3/44* | (2006.01) | |
| *G01V 3/30* | (2006.01) | |
| *G01V 8/02* | (2006.01) | |
| *G01V 11/00* | (2006.01) | |
| *G01N 21/65* | (2006.01) | |
| *E21B 47/06* | (2012.01) | |
| *G01V 3/38* | (2006.01) | |

(52) U.S. Cl.
CPC ............ *G01V 3/30* (2013.01); *E21B 47/06* (2013.01); *G01N 21/65* (2013.01); *G01V 3/38* (2013.01); *G01V 8/02* (2013.01); *G01V 11/00* (2013.01)

(58) Field of Classification Search
CPC . G01V 3/30; G01V 8/02; G01N 21/65; E21B 47/06; E21B 49/00
See application file for complete search history.

(56) References Cited

U.S. PATENT DOCUMENTS

| | | | | |
|---|---|---|---|---|
| 8,483,965 B2 * | 7/2013 | Bradley | ............... | G01V 11/00 702/1 |
| 2003/0048450 A1 | 3/2003 | Pope et al. | | |

(Continued)

OTHER PUBLICATIONS

Troy Cook, "Calculation of Estimated Ultimate Recovery for wells in continuous-type oil and gas accumulations of the Uinta-Piceance Province", 2003.*

(Continued)

*Primary Examiner* — Kara E Geisel
*Assistant Examiner* — Maurice Smith

(57) ABSTRACT

A method of evaluating a shale source rock formation comprising: determining in situ partial pressures of a light hydrocarbon utilizing a downhole Raman tool and producing a map of spatial and vertical variations of the in situ partial pressures of the light hydrocarbon in the shale source rock formation.

6 Claims, 2 Drawing Sheets

(56) References Cited

U.S. PATENT DOCUMENTS

| | | |
|---|---|---|
| 2004/0061858 A1 | 4/2004 | Pope et al. |
| 2010/0228485 A1 | 9/2010 | Betancourt et al. |
| 2011/0036146 A1 | 2/2011 | Pope et al. |
| 2011/0106451 A1 | 5/2011 | Christy et al. |
| 2012/0227960 A1* | 9/2012 | Pope .................... E21B 43/006 166/250.01 |
| 2012/0312530 A1 | 12/2012 | Pope et al. |
| 2013/0113480 A1 | 5/2013 | Kadayam et al. |

OTHER PUBLICATIONS

International Search Report dated Mar. 2, 2015 of PCT/US2014/058165 filed Sep. 30, 2014.

* cited by examiner

METHODS FOR ESTIMATING RESOURCE DENSITY BY INTEGRATING SEISMIC METHODS WITH FLUID DENSITY AND PRESSURE IN SHALE RESOURCE PLAYS

RELATED CASES

This application claims the benefit of U.S. Provisional Application No. 61/885,225, filed on Oct. 1, 2013, which is incorporated herein by reference.

BACKGROUND

The present disclosure relates generally to methods for estimating the in situ density of light hydrocarbons. More specifically, in certain embodiments, the present disclosure relates to methods for estimating in situ density of light hydrocarbons in shale source rock vein and matrix minerals using Raman spectroscopy and associated methods.

One of the objectives of an exploration and appraisal campaign in unconventional shale gas and liquid rich shale plays is to "sweet spot" the acreage in terms of potential estimated ultimate recovery (EUR). Sweet spotting is a term used to refer to the identification of the top quartile wells in a given production zone. This is often difficult to do in the absence of reliable production data. Estimating EUR in shale gas formations is especially challenging since EUR is a dynamic production metric while all other rock properties being measured are static in-situ properties. The relationship between these different states is not intuitive and presently poorly understood. In order to successfully sweet spot an unconventional shale source rock play, an estimate of the mass of light hydrocarbon per volume of source rock (i.e. the in situ density of light hydrocarbon) is required.

It is desirable to develop a method of determining in situ density and pressure of light hydrocarbons in a gas-bearing shale source rock in order to develop accurate EUR maps and identify sweet spots in the shale source rock formations.

SUMMARY

The present disclosure relates generally to methods for estimating the in situ density of light hydrocarbons. More specifically, in certain embodiments the present disclosure relates to methods for estimating in situ density of light hydrocarbons in shale source rock vein and matrix minerals using Raman spectroscopy and associated methods.

In one embodiment, the present disclosure provides a method of evaluating a shale source rock formation comprising: determining in situ partial pressures of a light hydrocarbon utilizing a downhole Raman tool and producing a map of spatial and vertical variations of the in situ partial pressures of the light hydrocarbon in the shale source rock formation.

In another embodiment, the present disclosure provides a method of evaluating a shale source rock formation comprising: determining in situ partial pressures of a light hydrocarbon utilizing a downhole Raman tool; producing a map of spatial and vertical variations of proxies for pressure normalized-estimated ultimate recovery; and identifying the areas on the map that correspond to a top quartile for pressure normalized-estimated ultimate recovery.

BRIEF DESCRIPTION OF THE DRAWINGS

A more complete and thorough understanding of the present embodiments and advantages thereof may be acquired by referring to the following description taken in conjunction with the accompanying drawings.

Figure 1:
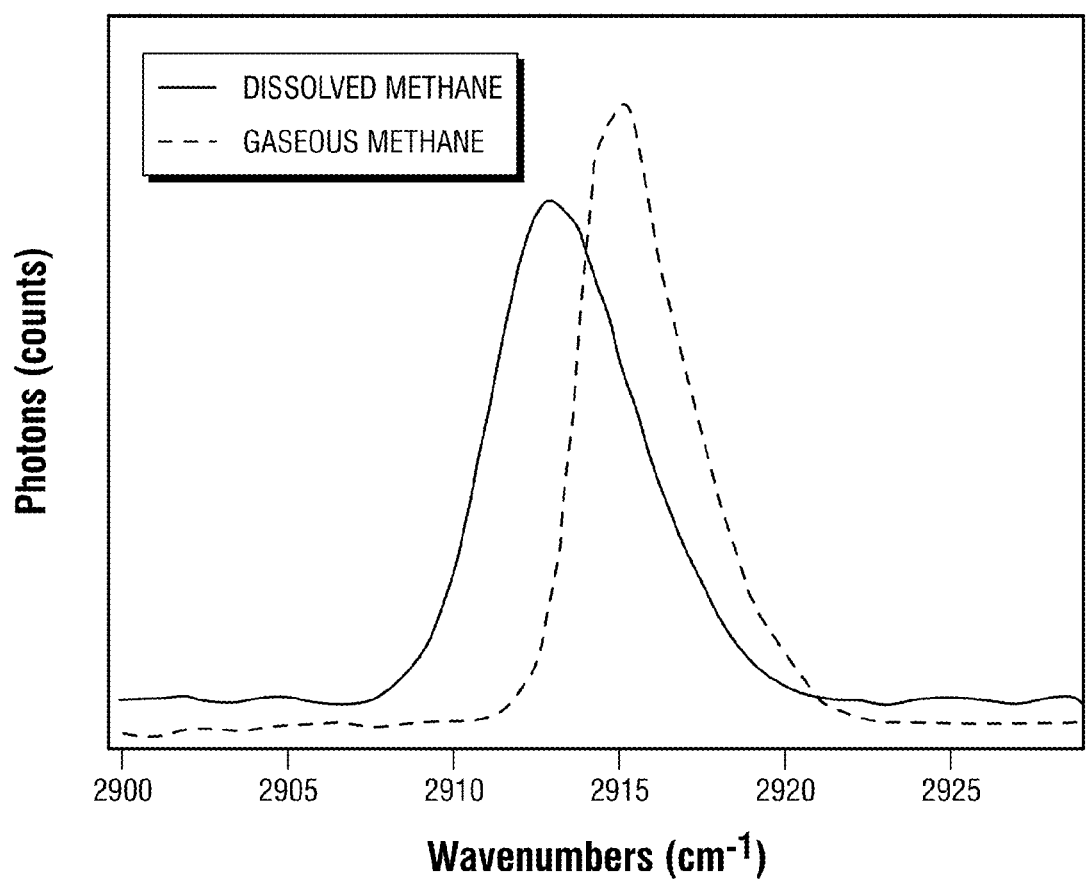
FIG. 1 is a chart depicting the relationship between pressure and concentration of light hydrocarbons.

The features and advantages of the present disclosure will be readily apparent to those skilled in the art. While numerous changes may be made by those skilled in the art, such changes are within the spirit of the disclosure.

DETAILED DESCRIPTION

The description that follows includes exemplary apparatuses, methods, techniques, and/or instruction sequences that embody techniques of the inventive subject matter. However, it is understood that the described embodiments may be practiced without these specific details.

The present disclosure relates generally to methods for estimating the in situ density of light hydrocarbons. More specifically, in certain embodiments the present disclosure relates to methods for estimating in situ density of light hydrocarbons in shale source rock vein and matrix minerals using Raman spectroscopy and associated methods.

Some desirable attributes of the methods discussed herein are that they are more accurately able to predict areas and volumes of organic rich source rocks with favorable estimated ultimate recovery attributes. By measuring the pressure and density of light gases in an organic-rich shale source rock formation, it is possible to produce more accurate maps of estimated ultimate recovery for sweet spotting purposes than conventional methods. Sweet spotting may be achieved by mapping in two dimensions estimated ultimate recovery data and making a map that then can highlight the most favorable part of a basin/play/prospect for early development based on the spatial distribution of resource density i.e. the density of hydrocarbon per volume of rock.

In certain embodiments, this disclosure outlines methods for evaluating the densities of light hydrocarbons generated by organic rich source rock shale. These methods may be based on the association of light hydrocarbon concentrations of dissolved components measured downhole using a wireline conveyed Raman tool. A strong correlation between the densities of the light hydrocarbon generated by a shale source rock and estimated ultimate recovery, specifically the pressure normalized-estimated ultimate recovery, has previously been observed. Because of this correlation, the in situ densities and pressures of the light hydrocarbon at various points in the formation may be inferred from an Equation of State model and the measured concentration of light hydrocarbons dissolved in water in a borehole penetrating an organic rich source rock interval. The in situ densities and pressures are recognized proxies for pressure normalized-estimated ultimate recovery data that is normally obtained from production data.

In one embodiment, the present disclosure provides a method of evaluating a shale source rock formation comprising: determining in situ partial pressures of a light hydrocarbon utilizing a downhole Raman tool and producing a map of spatial and vertical variations of the in situ partial pressures of the light hydrocarbon in the shale source rock formation.

In certain embodiments, the light hydrocarbon may be any hydrocarbon which is a gas at standard pressure and temperature conditions. Suitable examples of light hydrocarbons include methane, ethane, propane, butane, pentane, or any combination thereof.

In certain embodiments, the shale source rock formation may be a recognized source rock based on its total organic carbon (TOC) content. In other embodiments, the shale source rock formation may be an organic-rich shale source rock formation comprising a natural gas liquid resource as the dominant hydrocarbon species. Regardless of the particular type of shale source rock formation, the total pressure of the light hydrocarbons at a particular location in the shale source rock formation may be a summation of all of the partial pressures of gas components present and individual species partial pressures at that particular location and thus may still serve as a valid proxy for the pressure normalized-estimated ultimate recovery of any of the component hydrocarbon species present in the formation of interest.

In certain embodiments, the in situ pressure and composition of the light hydrocarbon may be determined by utilizing a downhole Raman tool. In certain embodiments, the downhole Raman tool may be used to measure dissolved concentrations of light hydrocarbons dissolved in water occupying a borehole volume adjacent to an organic rich source rock. An example of a suitable downhole Raman tool in one developed by WellDog. Other examples of such tools are described in U.S. Patent Application Publication Nos. 2012/0312530, 2011/0036146, 2004/0061858, and 2003/0048450, the entireties of which are hereby incorporated by reference.

Briefly, in certain embodiments, the downhole Raman tool is capable of measuring the intensity of C-H vibrational modes using a laser to excite photons in a mixture of water and light hydrocarbons. As water does not have a Raman response in the frequency that excited photons are produced by the characteristic light hydrocarbon vibrational models, the Raman response may be used to measure the concentration of light hydrocarbon gas dissolved in a water saturated borehole environment. An example of a Raman response used to measure the concentration of methane solution gas in the water saturated borehole environment is shown in FIG. 1. As can be seen in FIG. 1, the peak Raman response of gaseous methane is around 2915 cm-1 while the peak Raman response of dissolved methane is around 2913 cm-1.

In certain embodiments, in order to estimate the in situ partial pressure of a light hydrocarbon utilizing a downhole Raman tool, a section of the bore hole may have to be isolated. One method of isolating the bore hole includes using rubber packers inflated with water to seal off a selected length of vertical well bore. In such a system, because the system may be under a hydraulic head, the pressure within the packed off interval may be equal to the hydrostatic pressure of water. In situ temperature may be recorded using a thermocouple and the water salinity may be estimated by measuring the resistivity of the fluid in the packed off borehole interval.

In other embodiments, the section of the borehole may be left un-isolated and un-packed when utilizing the downhole Raman tool.

The light hydrocarbon response from the Raman tool measures peak intensity of the characteristic light hydrocarbon Raman peaks. These peaks can be compared to previously calibrated peaks to determine the concentration of light gases dissolved in water in the well bore. The partial pressures of the light gases may then be calculated utilizing an appropriate Henry's Law constant. In embodiments where the shale source rock formation contains only one type of light hydrocarbons (e.g. only methane) a single Equation of State model for that light hydrocarbon may be used to calculate the pressure in the formation at the location where the downhole Raman tool measured the light hydrocarbon. In embodiments where the shale source rock formation contains a mixture of light hydrocarbons or other gases, other more suitable Equations of State for mixtures may be used to calculate the partial pressure of each light hydrocarbon or gas and the overall pressure of the mixture. Conversely, a single Equation of State model may be used for mixtures of gases, requiring only the use of thermodynamically established mixing laws for the different components comprising the gas phase. In certain embodiments, commercially available PVT simulation software packages may be used to calculate the pressure of the light hydrocarbon based upon the measured concentration of the light hydrocarbon.

Temperature may be determined from direct measurement in the well bore. For example, in certain embodiments, the downhole Raman tool may comprise a thermocouple that measures the temperature.

Thus, by using the methods discussed above, the pressures of a light hydrocarbon in a formation at locations where the downhole Raman spectroscopy was performed may be estimated.

In certain embodiments producing a map of the spatial and vertical variations of the in situ partial pressures of the light hydrocarbon in the shale source rock formation may comprise using a downhole Raman device to determine in situ partial pressures of a light hydrocarbon at multiple locations in the shale source rock formation and using these estimates, preparing a map depicting the spatial and vertical variations of the partial pressures of the light hydrocarbons may be produced. The pressures of the light hydrocarbons at other locations not measured may be estimated using conventional interpolation and/or extrapolation techniques.

In certain embodiments, the present disclosure provides a method of evaluating a shale source rock formation comprising: determining in situ partial pressures of light hydrocarbons utilizing a downhole Raman tool; producing a map of spatial and vertical variations of proxies for pressure normalized-estimated ultimate recovery; and identifying potential areas on the map that correspond to a top quartile for pressure normalized-estimated ultimate recovery In certain embodiments, the map predicting the spatial and vertical variation of pressure normalized-estimated ultimate recovery may be produced relying solely on the data obtained from any of the methods discussed above. In certain embodiments, the map predicting the spatial and vertical variation of pressure normalized-estimated ultimate recovery may be produced relying on a combination of the methods discussed above and any other methods. The in situ pressures of the light hydrocarbons may then be mapped and the areas with top quartile potential may be identified. Typically, the best producing intervals of the formation correlate with the pressure normalized-estimated ultimate recovery. Thus, in situ density and/or pressure may be used as a proxy for pressure normalized-estimated ultimate recovery.

In certain embodiments, producing the map of the spatial and vertical variation of proxies for pressure normalized-estimated ultimate recovery may comprise using the calculated partial pressures of various light hydrocarbon components as proxies for pressure normalized-estimated ultimate recovery at each of those locations and preparing a map based upon these proxies. In certain embodiments, these proxies may also be calculated based upon formation properties such as Total Organic Carbon, porosity, gas composition, and pressure, temperature, and volume properties of the light hydrocarbons.

The formation properties may be determined in a variety of ways. In certain embodiments, a variety of these formation properties, for example, gas composition, partial pressure, temperature, and/or volume, may be determined using any of the methods described above.

In certain embodiments, other formation properties at multiple locations may be calculated using seismic data such as acoustic and elastic impendence of the subsurface formation using an inversion algorithm. An example of a seismic inversion algorithm may include the following steps: (1) seed an initial subsurface model with an initial estimate of the subsurface acoustic and elastic impedances, (2) generate a synthetic systemic response based on the initial estimate using a forward modeling algorithm that simulates the dependence of seismic properties on variation in acoustic and elastic impedances, and (3) compare the synthetic data with the actual seismic data. When comparing the synthetic data with the actual seismic data, if the error is acceptably small the initial estimate may be accepted as the final result. On the other hand, if the error is unacceptably large, the subsurface model may be perturbed in a manner that can improve agreement with the measured data and then steps (2) and (3) may be repeated until the error is acceptably small and convergence is obtained. This final model may then be used to produce the pressure normalized-estimated ultimate recovery maps.

After an agreement of synthetic data and field data is reached the inverted seismic properties may be used to calculate formation properties. Several additional calibration steps may be involved to determine formation properties for unconventional reservoirs compared to conventional formations. The acoustic properties of the organic matter and kerogen may have to be established by using methods such as nanoindentation of the organic matter in order to estimate mechanical and elastic properties. With these properties established, the inverted acoustic properties may then be used to estimate to volume of organic matter and bulk density of the formation. A map of the thickness of the reservoir interval in the area of interest may then be generated using these results.

To convert a bulk density into porosity, the density of the organic matter and/or kerogen may need to be known. The maturity of the kerogen may be determined by using Raman measurement of solid organic matter and then estimating a ratio of the D5/G peak ratio, where D5 and G refer to characteristic Raman peaks of organic components in the solid organic matter, specifically the aliphatic C-C stretch vibrational mode (D5) and the bulk aromatic or grapheme like component (G). The grain density of the organic matter may then be estimated based on the maturity of the kerogen and a proprietary correlation between maturity and the grain density of solid organic matter. Using the volume and density of the organic matter and the bulk density of the rock mineral matrix, the porosity of the formation may then be estimated. A map of the average porosity of the reservoir interval in the area of interest may then be generated using these results.

Figure 2:
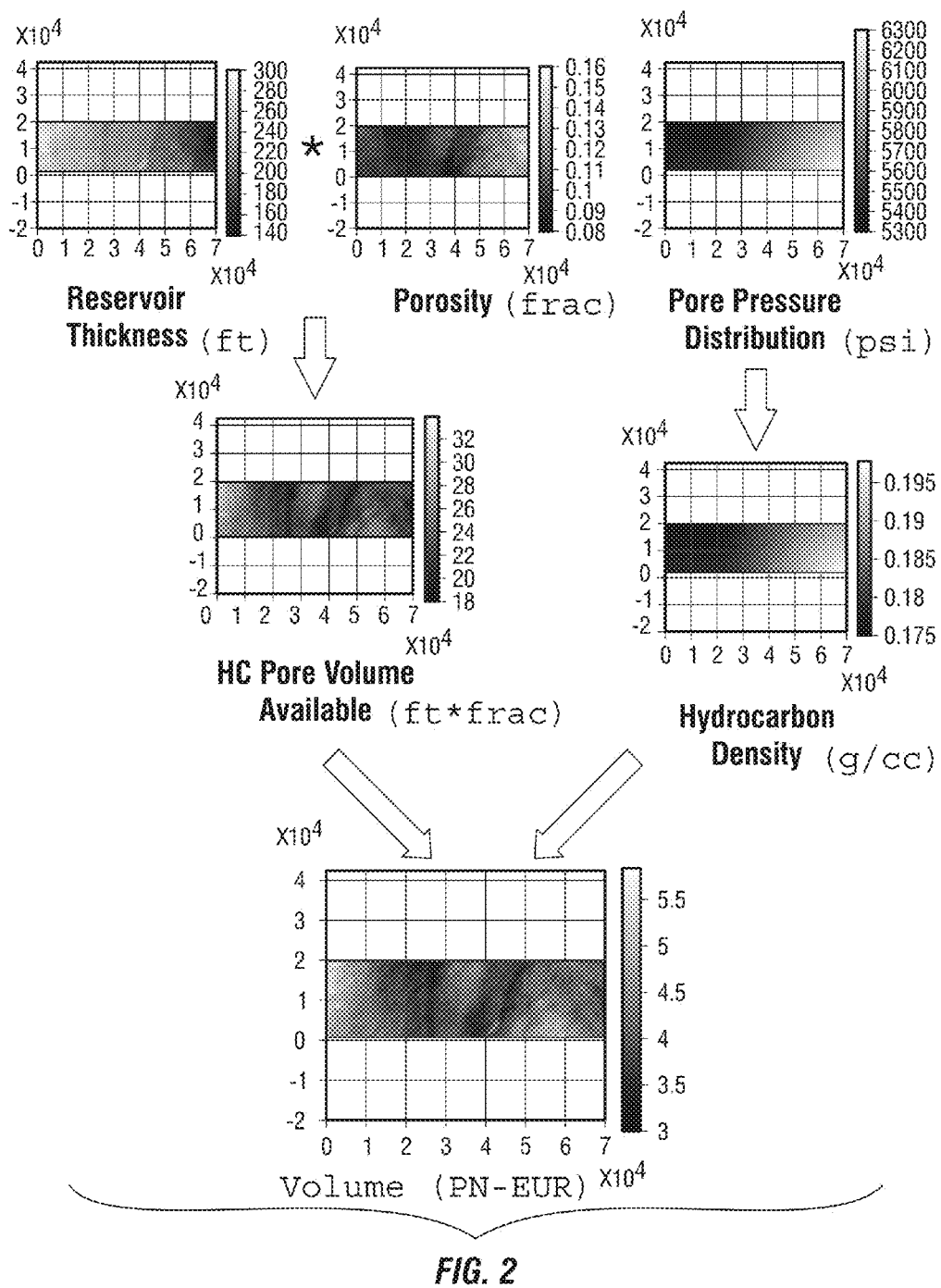
FIG. 2 is an illustration of the convolution of various aerial distributions of reservoir data to create an aerial distribution of hydrocarbon volume and proxy PN-EUR.

The maps of the thickness of the reservoir internal and the average porosity of the reservoir interval may then be convolved to generate a map of the distribution of the potential pore space volume of the reservoir interval in the area of interest. The map depicting the spatial and vertical variations of the partial pressures of the light hydrocarbons may then be convolved with the map of the distribution of the potential pore space volume to produce a pressure normalized-estimated ultimate recovery map. Using this data, a map that predicts the spatial and vertical variations of estimated ultimate recovery may be produced and the areas on that map may then be identified as having the potential to be top quartile candidates for development. FIG. 2 illustrates the convolution of these maps. As can be seen in FIG. 2, the lighter colored areas of each map correspond to higher values of thickness, porosity, pore space, partial pressure, hydrocarbon density, and estimated ultimate recovery.

While the embodiments are described with reference to various implementations and exploitations, it will be understood that these embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method of evaluating a shale source rock formation comprising:
determining in situ partial pressures of a light hydrocarbon utilizing a downhole Raman tool;
producing a map of spatial and vertical variations of proxies for pressure normalized-estimated ultimate recovery; and
identifying the areas on the map that correspond to a top quartile for pressure normalized-estimated ultimate recovery;
wherein producing a map of spatial and vertical variations of proxies for pressure normalized-estimated ultimate recovery comprises:
producing a map of spatial and vertical variations of the partial pressures of the light hydrocarbons;
producing a map of the distribution of the potential pore space volume; and
convolving the map of spatial and vertical variation of the partial pressures of the light hydrocarbons and the map of the distribution of the potential pore space volume to produce a map of the spatial and vertical variation of proxies for pressure normalized-estimated ultimate recovery.

2. The method of claim 1, wherein the light hydrocarbon comprises methane, ethane, propane, butane, or any combination thereof.

3. The method of claim 1, wherein the proxies for pressure normalized-estimated ultimate recovery are the in situ pressures and densities of the light hydrocarbon.

4. The method of claim 1, wherein producing a map of the distribution of the potential pore space volume comprises:
producing a map of the thickness of a reservoir interval;
producing a map of the average porosity of the reservoir interval;
convolving the map of the thickness of the reservoir interval and the map of the average porosity of the reservoir interval to produce the map of the distribution of the potential pore space volume.

5. The method of claim 4, wherein producing a map of the thickness of the reservoir interval comprise: using inverted acoustic properties to estimate to volume of organic matter and bulk density of the formation.

6. The method of claim 4, wherein producing the map of the average porosity of the reservoir interval comprises: measuring a volume and density of organic matter in the reservoir interval and using the volume and density of the organic matter and the bulk density of the rock mineral matrix to estimate the porosity of the reservoir interval.

* * * * *